United States Patent [19]

Lindner et al.

[11] 4,292,434

[45] Sep. 29, 1981

[54] PROCESS FOR THE ADDITION OF SI-BONDED HYDROGEN TO AN ALIPHATIC MULTIPLE BOND

[75] Inventors: Tassilo Lindner, Mehring-Öd, Fed. Rep. of Germany; Georg Engelsberger, Ach, Austria; Norbert Zeller; Rudolf Riedle, both of Burghausen, Fed. Rep. of Germany

[73] Assignee: Wacker-Chemie GmbH, Munich, Fed. Rep. of Germany

[21] Appl. No.: 205,140

[22] Filed: Nov. 10, 1980

[30] Foreign Application Priority Data

Jan. 10, 1980 [DE] Fed. Rep. of Germany ....... 3000768

[51] Int. Cl.$^3$ .............................................. C07F 7/08
[52] U.S. Cl. ................................. 556/479; 252/431 N
[58] Field of Search .......................................... 556/479

[56] References Cited

U.S. PATENT DOCUMENTS

| | | | |
|---|---|---|---|
| 3,057,902 | 10/1962 | Pike | 556/479 |
| 3,099,670 | 7/1963 | Prober | 556/479 X |
| 3,153,662 | 10/1964 | Pike | 556/479 |
| 3,159,662 | 12/1964 | Ashby | 556/479 X |
| 3,178,464 | 4/1965 | Pierpoint | 556/479 X |
| 3,410,886 | 11/1968 | Joy | 556/479 |
| 3,925,434 | 12/1975 | Chuang | 556/479 X |

FOREIGN PATENT DOCUMENTS

923710 4/1963 United Kingdom ............... 556/479

*Primary Examiner*—Paul F. Shaver

[57] ABSTRACT

A process for the addition of Si-bonded hydrogen to an aliphatic multiple bond in the presence of a platinum catalyst which is obtained by dissolving a platinum halide in at least 20 parts by weight of olefin for each part by weight of the platinum halide, and subsequently heating and mixing the solution obtained with from 0.5 to 1 mole of a primary and/or secondary amine for each gram atom of platinum.

6 Claims, No Drawings

PROCESS FOR THE ADDITION OF SI-BONDED HYDROGEN TO AN ALIPHATIC MULTIPLE BOND

The present invention relates to platinum catalysts and more particularly to platinum catalysts which may be used to promote the addition of Si-bonded hydrogen to an aliphatic multiple bond.

BACKGROUND OF THE INVENTION

It has been known that the addition of Si-bonded hydrogen to an aliphatic multiple bond, often referred to as "hydrosilylization", can be promoted with platinum catalysts. For example, U.S. Pat. No. 3,798,252 to Nitzsche et al discloses the addition of Si-bonded hydrogen to aliphatic multiple bonds in the presence of a platinum catalyst which is obtained from the reaction of chloroplatinic acid and ketones.

Although U.S. Pat. No. 3,188,299 to Chalk teaches that platinum compositions containing a nitrogen ligand inhibit the addition of the Si-bonded hydrogen to an aliphatic multiple bond at room temperature, applicants have found that even though the platinum-containing catalysts of this invention contain basic nitrogen compounds, they are more effective and more reactive even at room temperature, i.e., they have shorter induction times than other platinum catalysts which promote the addition of Si-bonded hydrogen to an aliphatic multiple bond. Another important advantage of this invention is that less time is required between the initiation and termination of the hydrosilylization reaction, i.e., the reaction proceeds at a much faster rate with the platinum-containing compositions of this invention. Still another advantage of this invention is that lower concentrations of platinum and/or the platinum-containing compositions of this invention are required and they are more effective over a longer period of time. Furthermore, the platinum-containing catalysts of this invention do not promote polymerization of the initial reactants and the formation of undesired end products.

Therefore, it is an object of this invention to provide a platinum catalyst which will promote the addition of Si-bonded hydrogen to an aliphatic multiple bond. Another object of this invention is to provide a platinum catalyst which is more effective at room temperature. Another object of this invention is to provide a platinum catalyst which is more reactive at room temperature. Still another object of this invention is to provide a platinum catalyst which is more effective even at lower concentrations. A further object of this invention is to provide a platinum catalyst which is more effective over a longer period of time. A still further object of this invention is to provide a platinum catalyst which does not promote polymerization of the initial reactants and the formation of undesired end products.

SUMMARY OF THE INVENTION

The foregoing objects and others which will become apparent from the following description are accomplished in accordance with this invention, generally speaking, by providing a platinum catalyst solution which promotes the addition of Si-bonded hydrogen to an aliphatic multiple bond in which the platinum catalyst is prepared by dissolving a platinum halide in at least 20 parts by weight of olefin for each part of the platinum halide and thereafter heating and mixing the solution with from 0.5 to 1 mole of a primary and/or secondary amine for each gram atom of platinum.

DETAILED DESCRIPTION OF THE INVENTION

The platinum halides which may be used in preparing the catalyst solution of this invention consist of platinum and halogen atoms and optionally, hydrogen and oxygen atoms. Examples of platinum halides which may be used in the preparation of the platinum-containing composition of this invention are platinum dichloride, platinum dibromide and chloroplatinic acid ($H_2PtCl_6.6H_2O$). It is possible to use just one type of platinum halide, but a mixture containing various types of platinum halides, for example platinum tetrachloride and chloroplatinic acid may be used. The preferred platinum halide is platinum tetrachloride.

It is preferred that the olefin contain from 6 to 18 carbon atoms per molecule and consist of only carbon and hydrogen atoms. More preferably the olefin is a linear or branched octene. Examples of suitable octenes are 1-octene, cis-2-octene and dimerized 1-butene. Other examples of olefins which may be used in the preparation of the catalyst compositions of this invention are linear or branched mono-olefins having at least 6 carbon atoms, other than the octenes, such as for example 1-nonene, 2-nonene, 1-heptene, 1-dodecene and 6-dodecene as well as diolefins and polyolefins having at least 6 carbon atoms, such as, 1,4-hexadiene and 1,5-cyclooctadiene. Olefins having from 2 to 5 carbon atoms may be used when pressure is employed in the preparation of the catalyst compositions.

In preparing the platinum-containing compositions of this invention, it is possible to use either a single type of olefin or mixtures of various olefins, for example various octene isomers or olefins containing various numbers of carbon atoms.

In preparing the platinum containing compositions of this invention, it is preferred that from 100 to 2,000 parts by volume of olefin be employed for each part by weight of the platinum halide.

The platinum catalysts are preferably prepared by dissolving platinum halide in at least 20 parts by weight of olefin for each part by weight of platinum halide and the resultant mixture may be heated from 10 minutes to 5 hours at 60° to 120° C. The olefin reacts with the platinum halide to form a platinum-olefin complex. The platinum-olefin complex is then mixed with from 0.5 to 1 mole of a primary and/or secondary amine per gram atom of platinum and the resultant solution is preferably heated from 40° to 100° C. over a period of from 10 minutes up to about 2 hours.

The terms "primary" and "secondary" amines refer to basic organic nitrogen compounds in which each nitrogen atom carries one or two hydrogen atoms and the nitrogen valences which are not saturated by hydrogen atoms are saturated by monovalent or bivalent carbon atoms which may optionally be substituted with either oxygen atoms or hydroxyl groups.

It is preferred that the amines used in the preparation of the platinum-containing compositions of this invention have from 1 to 15 carbon atoms for each organic radical that is bonded to the nitrogen atom. Examples of suitable amines which may be used in preparing the catalyst compositions of this invention are methylamine, dimethylamine, ethylamine, n-propylamine, isopropylamine, n-butylamine, sec-butylamine, cyclohexylamine, aniline, p-toluidine, ethylenediamine, morpholine and diethanolamine, with sec-butylamine being the preferred amine.

In preparing the platinum-containing compositions of this invention, it is possible to use a single type of amine or a mixture of various types of amines, for example a mixture containing sec-butylamine and cyclohexylamine.

The platinum halide may be dissolved in the olefin and the solution containing the amine may be heated at atmospheric pressure or at lower or higher pressures.

The amount of catalyst used to promote the addition of Si-bonded hydrogen to an aliphatic multiple bond may be the same amount as was used heretofore to promote the addition of Si-bonded hydrogen to an aliphatic multiple bond in the presence of a platinum catalyst. However, an amount of from $10^{-7}$ to $10^{-3}$ gram atom of platinum, calculated as elemental platinum, per gram atom of Si-bonded hydrogen, is preferred.

Temperatures and pressures which have been used heretofore in promoting the addition of Si-bonded hydrogen to an aliphatic multiple bond may be used in the process of this invention in promoting the addition of Si-bonded hydrogen to an aliphatic multiple bond in the presence of the platinum catalyst. Although, temperatures between 18° and 150° C. and atmospheric pressure (i.e., 1 bar or approx. 1 bar) are preferred, higher or lower pressures may be used as well.

The catalyst composition of this invention may be used whenever monomeric or polymeric silicon compounds having Si-bonded hydrogen are to be added to monomeric or polymeric compounds having an aliphatic multiple bond. Depending on the compounds employed in the addition, other monomeric silicon compounds or dimeric or polymeric silicon-containing compounds may be formed.

Examples of monomeric silicon compounds which may be formed using the catalyst composition of this invention are 3-chloropropyltrichlorosilane from the reaction of trichlorosilane with allyl chloride, 3-chloropropylmethyldichlorosilane from the reaction of methyldichlorosilane with allylchloride, n-propyltrichlorosilane from the reaction of propene with trichlorosilane, gamma-methacryloxypropyltrichlorosilane from the reaction of allylmethacrylate with trichlorosilane and vinylmethyldichlorosilane from the reaction of acetylene with methyldichlorosilane. It is preferred that the process of this invention may be used to prepare monomeric organosilicon compounds.

Dimeric and polymeric Si-containing compounds which may be prepared by the process of this invention are bis(1,2-trichlorosilyl)-ethane by reacting vinyltrichlorosilane with trichlorosilane and organosiloxanes having SiC-bonded ester groups by the addition of at least one diester of allylsuccinic acid to an organosiloxane having Si-bonded hydrogen.

The process of this invention may be used to modify polymeric silicon containing compounds by crosslinking, i.e., curing or vulcanizing compositions containing alkenyl groups, especially vinyl groups and organopolysiloxanes which contain Si-bonded hydrogen. Such compositions may be used, for example, as potting compounds for electrical or electronic devices or they may be used for coatings, including coatings which repel adhesive substances, for example, as paper coating or they may be used as mold release agents, for example as release agents in molding objects from concrete, or for obtaining impressions of human or animal teeth.

Agents which retard the addition of Si-bonded hydrogen to an aliphatic multiple bond, may be used in the compositions of this invention. Examples of suitable agents are benzotriazole, 1,3-divinyl-1,1,3,3-tetramethyldisiloxane and/or 2-methyl-3-butine-2-ol.

EXAMPLE 1

To an insulated vessel containing 0.5 mole of trichlorosilane and 0.5 mole allylmethacrylate is added a platinum catalyst in an amount such that $5 \cdot 10^{-6}$ gram atom of platinum is present.

The platinum catalysts used in the above example are prepared in the following manner:

(a) The platinum catalyst of this invention was prepared by heating 27.5 g platinum tetrachloride in 1.6 liters of 1-octene for 2 hours at 100° C., then adding 3.1 ml of sec-butylamine to one liter of the solution, which corresponds to 0.6 mole per gram atom of platinum and thereafter heating the solution at 60° C. for 1 hour.

(b) Comparison Example $V_1$

A solution was prepared by heating 27.5 g platinum tetrachloride in 1.6 liters of 1-octene for 2 hours at 100° C.

(c) Comparison Example $V_2$

A catalyst solution was prepared in accordance with U.S. Pat. No. 3,798,252, Example 1(c) in which a solution containing 1 g of chloroplatinic acid in 200 ml of cyclohexanone is heated to 100° C. for 1 hour and thereafter the solution is dried over anhydrous sodium sulfate.

The addition of the catalysts is followed by an increase in temperature which is attributable to the exothermic addition of trichlorosilane to allylmethacrylate. The rapid increase in temperature is an indication of the speed of the addition reaction and thus an indicator of the catalyst's activity. The results are shown in Table 1.

Using the catalyst composition of this invention, the addition is complete as indicated by the maximum temperature attained after 3 minutes and with essentially complete conversion of the trichlorosilane.

TABLE 1

| Cata- | Temperature in °C. after number of minutes Minutes | | | | | | | | | | | | | | |
|---|---|---|---|---|---|---|---|---|---|---|---|---|---|---|---|
| lyst | 0 | 1 | 2 | 3 | 5 | 6 | 8 | 10 | 12 | 15 | 18 | 21 | 24 | 27 | 30 |
| (a) | 21° | 70° | 136° | 139° | | | | | | | | | | | |
| ($V_1$) | 21° | 22° | | 23° | | | | | | | | | 24° | | |
| ($V_2$) | 21° | 23° | | 24° | 25° | 26° | 28° | 30° | 33° | 39° | 60° | 69° | 82° | 100° | 112° |

EXAMPLE 2

The process described in Example 1 is repeated, except that 0.5 mole of allylchloride is substituted for the 0.5 mole of allylmethacrylate and $5 \cdot 10^{-5}$ gram atom of platinum is used instead of $5 \cdot 10^{-6}$ gram atom of platinum. The results are shown in Table 2.

TABLE 2

| Cata-lyst | Temperature in °C. after minutes Minutes | | | | | | | | | | | | | |
|---|---|---|---|---|---|---|---|---|---|---|---|---|---|---|
| | 0 | 1 | 2 | 3 | 4 | 5 | 6 | 7 | 8 | 9 | 10 | 13 | 14 | 30 |
| (a) | 20° | 25° | 45° | 57° | 75° | 84° | 87° | | | | | | | |
| (V₁) | 20° | 23° | 24° | 25° | 26° | 27° | 28° | | 29° | | 30° | | 32° | 34° |
| (V₂) | 20° | 39° | 41° | 44° | 47° | 51° | 55° | 59° | 63° | 68° | 72° | 78° | 79° | |

Gas chromotographic analysis reveals that the product prepared in accordance with this invention has the following composition:

3-chloropropyltrichlorosilane: 76 percent by weight
propyltrichlorosilane: 5 percent by weight
allylchloride: 2 percent by weight
SiCl$_4$: 15 percent by weight
trichlorosilane: 0 percent by weight

What is claimed is:

1. An improved process for the addition of Si-bonded hydrogen to an aliphatic multiple bond in the presence of a platinum catalyst, the improvement which comprises carrying out said addition reaction in the presence of a catalyst solution obtained from the reaction of a platinum halide with at least 20 parts by weight of olefin for each part by weight of platinum halide, and thereafter heating the resultant solution with from 0.5 to 1 mole of an amine selected from the group consisting of a primary and secondary amine for each gram atom of platinum.

2. The improved process of claim 1, wherein the platinum halide may also contain hydrogen and oxygen atoms.

3. The improved process of claim 1, wherein the halide is platinum tetrachloride.

4. The improved process of claims 1 or 3, wherein the solution obtained from the reaction of the platinum halide with at least 20 parts by weight of olefin for each part by weight of platinum, is heated to a temperature of from 60° to 120° C. for from 10 minutes to 5 hours.

5. The improved process of claims 1 or 3, wherein the amine is a sec-butylamine.

6. The improved process of claims 1 or 3, wherein the solution obtained from the reaction of a platinum halide is mixed with from 0.5 to 1 mole of an amine selected from the group consisting of primary and secondary amines per gram atom of platinum and heated at a temperature of from 40° to 100° C. over a period of from 10 minutes to 2 hours.

* * * * *